(12) United States Patent
Lin

(10) Patent No.: US 10,572,865 B2
(45) Date of Patent: *Feb. 25, 2020

(54) GAS VENDING SYSTEM FOR HEALTH APPLICATION

(71) Applicant: Hsin-Yung Lin, Shanghai (TW)

(72) Inventor: Hsin-Yung Lin, Shanghai (TW)

( * ) Notice: Subject to any disclaimer, the term of this patent is extended or adjusted under 35 U.S.C. 154(b) by 0 days.

This patent is subject to a terminal disclaimer.

(21) Appl. No.: 15/889,050

(22) Filed: Feb. 5, 2018

(65) Prior Publication Data

US 2018/0158038 A1    Jun. 7, 2018

Related U.S. Application Data

(63) Continuation of application No. 14/508,383, filed on Oct. 7, 2014, now Pat. No. 9,928,492.

(30) Foreign Application Priority Data

Oct. 8, 2013   (CN) .......................... 2013 1 0464565

(51) Int. Cl.
| | |
|---|---|
| *G07F 15/02* | (2006.01) |
| *G06Q 20/18* | (2012.01) |
| *G07F 17/00* | (2006.01) |
| *C25B 1/02* | (2006.01) |
| *C25B 15/02* | (2006.01) |

(Continued)

(52) U.S. Cl.
CPC .......... *G06Q 20/18* (2013.01); *A61M 16/101* (2014.02); *A61M 16/14* (2013.01); *C25B 1/02* (2013.01); *C25B 15/02* (2013.01); *G07F 13/025* (2013.01); *G07F 15/001* (2013.01); *G07F 17/0092* (2013.01); *G07F 17/18* (2013.01); *A61M 11/00* (2013.01); *A61M 21/02* (2013.01); *A61M 2021/0016* (2013.01); *A61M 2202/0208* (2013.01); *A61M 2205/3553* (2013.01); *A61M 2205/3584* (2013.01); *A61M 2205/3592* (2013.01); *A61M 2205/502* (2013.01); *A61M 2205/52* (2013.01); *A61M 2205/609* (2013.01);

(Continued)

(58) Field of Classification Search
CPC .... G07F 15/001; G07F 13/025; G07F 15/003; A61M 16/101

See application file for complete search history.

(56) References Cited

U.S. PATENT DOCUMENTS

| | | | | |
|---|---|---|---|---|
| 2,855,926 | A * | 10/1958 | Koppelman | ............. A62B 7/02 |
| | | | | 128/202.13 |
| 6,419,882 | B1 * | 7/2002 | Matthews | ................ A62B 7/02 |
| | | | | 194/241 |

(Continued)

*Primary Examiner* — Timothy R Waggoner
(74) *Attorney, Agent, or Firm* — Foster Garvey PC

(57) ABSTRACT

A gas vending system for health application, comprising: a healthy gas generator module, a control module, and a charging/payment module. The healthy gas generator module is used to generate a healthy gas. The control module is connected to the healthy gas generator module for monitoring the usage state of the healthy gas and generating a volume consumption signal for the healthy gas. The charging/payment module is connected to the control module for receiving the volume consumption signal for the healthy gas and then generating a toll after computing. The charging/payment module is adapted to accept cash or charging a debit card or credit card according to the toll.

6 Claims, 2 Drawing Sheets

(51) Int. Cl.
  *G07F 17/18* (2006.01)
  *G07F 13/02* (2006.01)
  *G07F 15/00* (2006.01)
  *A61M 16/14* (2006.01)
  *A61M 16/10* (2006.01)
  *A61M 11/00* (2006.01)
  *A61M 21/02* (2006.01)
  *A61M 21/00* (2006.01)

(52) U.S. Cl.
  CPC ............... *A61M 2205/6054* (2013.01); *A61M 2205/6063* (2013.01); *A61M 2205/8231* (2013.01)

(56) References Cited

U.S. PATENT DOCUMENTS

| | | | |
|---|---|---|---|
| 6,536,431 B1* | 3/2003 | Simler | A61M 16/10 |
| | | | 128/204.18 |
| 7,522,972 B1* | 4/2009 | Basped | G07F 17/18 |
| | | | 128/200.24 |
| 9,928,492 B2* | 3/2018 | Lin | G07F 17/18 |
| 2005/0048461 A1* | 3/2005 | Lahteenmaki | A61J 3/002 |
| | | | 435/3 |
| 2013/0035786 A1* | 2/2013 | Hyde | G07F 9/023 |
| | | | 700/232 |
| 2013/0206586 A1* | 8/2013 | Lin | C25B 15/02 |
| | | | 204/228.2 |

* cited by examiner

GAS VENDING SYSTEM FOR HEALTH APPLICATION

CROSS-REFERENCE TO RELATED APPLICATION

This is a continuation application of U.S. application Ser. No. 14/508,383 filed on Oct. 7, 2014, which claims the benefit of the filing date of China Patent Application No. 201310464565.0, filed on Oct. 8, 2013. Each of the foregoing applications are incorporated by reference as if fully set forth herein.

FIELD OF THE INVENTION

The present invention relates to a vending system, and more particularly, to a gas vending system for health application.

BACKGROUND OF THE INVENTION

People are always paying a great deal of attention on health developments. Many developments in medical technology are often targeted towards treating diseases and prolonging human life. Most of the treatments in the past are passive, which means that they only treat the disease when the disease occurs. These include methods such as operating, medicating, radiation therapy, convalescing chronic diseases, rehabilitation, corrective therapy, or even medical treatment for cancer. But in recent years, much of the research from medical experts are gradually moving towards preventive medical methods, such as research on healthy food, screening and preventing inherited diseases, which actively prevents diseases from occurring in the future. Because of this focus on prolonging human life, many anti-aging and anti-oxidation technologies including skin care products and anti-oxidation food/medicine are gradually being developed and have become increasingly popular to the general public.

In recent years, people have begun noticing the benefits of aromatherapy. Aromatherapy is a natural way to make people feel relaxed and become healthier. Essential oils are extracted from aromatic plants to act as a medium, which is then exposed to someone by using it for massaging, bathing, perfuming and so on. This method has existed since the ancient times of Egypt and is now gaining a lot of attention in Europe. In the prior art, people found that the plant's essential oils can reach into the deep tissue layers of skin, that is then absorbed by blood vessels and reaches organs that can only be treated through blood circulation.

Therefore, the present invention provides a novel gas vending system and device for health application. The generated healthy gas for health application makes people feel relaxed and is also suitable for medical treatment, while having anti-aging and anti-oxidation effects. The vending system of the present invention can provide a convenient usage interface, which allows users to use the present invention in a comfortable and convenient situation.

SUMMARY OF THE INVENTION

An object of the present invention is to provide a gas vending system for health application using an electrolyzing method to generate a healthy gas. The present invention comprises a member/user management module, used to completely record the usage state of the user to provide as references for the user or the manager of the system.

Another object of the present invention is to provide a gas vending system for health application having a charging/payment module. The present invention also allows the user to conveniently pay using their debit card or credit card as it is connected to the banking system through the Internet.

Another object of the present invention is to provide a gas vending system for health application having a multimedia device, used to provide a comfortable situation for the user when being used. The multimedia device can also be used to watch videos or surf the Internet.

According to one embodiment of the present invention, the present invention provides a gas vending system for health application, comprising: a healthy gas generator module, used to generate a healthy gas. A control module, connected to the healthy gas generator module for monitoring the usage state of the healthy gas and generating a volume consumption signal for the healthy gas. A charging/payment module, connected to the control module for receiving the volume consumption signal of the healthy gas and generating a toll after computing. The charging/payment module is adapted to accept cash or charge a debit card or a credit card according to the toll.

According to some embodiments of the present invention, the gas vending system for health application further comprises a user management module that is connected to the control module and adapted to receive a user input signal for altering the operations of the control module. According to one embodiment of the present invention, the gas vending system for health application further comprises a communication module that is connected to the user management module and adapted to connect with a database, used to receive the user input signal and then exchange information with the database. According to another embodiment of the present invention, the gas vending system for health application further comprises an identification module that is connected to the user management module and adapted to identify biological characteristics of a user in order to generate the user input signal. According to another embodiment of the present invention, the gas vending system for health application further comprises an input/output module, connected to the user management module and adapted to receive an input from the user and then generate the user input signal.

According to some embodiments of the present invention, the gas vending system for health application further comprises a display device that is connected to the control module. According to other embodiments of the present invention, the gas vending system for health application further comprises: a video/Internet module that is connected to the control module and the display device and adapted to provide a video output; and a communication module, connected to the video/Internet module, wherein the video/Internet module is connected to an Internet through the communication module.

According to one embodiment of the present invention, the gas vending system for health application further comprises a communication module, connected to the charging/payment module, wherein the charging/payment module is connected to a financial system through the communication module.

According to some embodiments of the present invention, the healthy gas generation module of the gas vending system for health application comprises: a hydrogen and oxygen generation module, a water filling module, and an atomized gas mixing module, wherein the hydrogen and oxygen generation module is used for generating hydrogen and oxygen through electrolyzing electrolyzed water, the water filling module is connected to the hydrogen and oxygen generation module for filling the electrolyzed water, and the atomized gas mixing module is connected to the hydrogen and oxygen generation module to receive the hydrogen and oxygen and then selectively mixing a atomized gas to generate the healthy gas.

According to the gas vending system for health application of the present invention, the user can be charged according to the volume consumption of the healthy gas through the charging/payment module. The charging/payment module is adapted to accept cash or charge a debit card or credit card. Additionally, the present invention can completely record the usage state of the user to provide as references for the user or the manager of the system through the user management module and communication module that is connected with the database. The gas vending system for health application of the present invention further comprises a video/Internet module and a display device, which allows the user to watch videos or surf the Internet in a comfortable situation while using the present invention.

The advantages and spirits of the invention may be understood by the following recitations together with the appended drawings.

BRIEF DESCRIPTION OF THE DRAWINGS

Preferred and alternative examples of the present invention are described in detail below with reference to the following drawings:

DETAILED DESCRIPTION OF THE DRAWINGS

Figure 1:
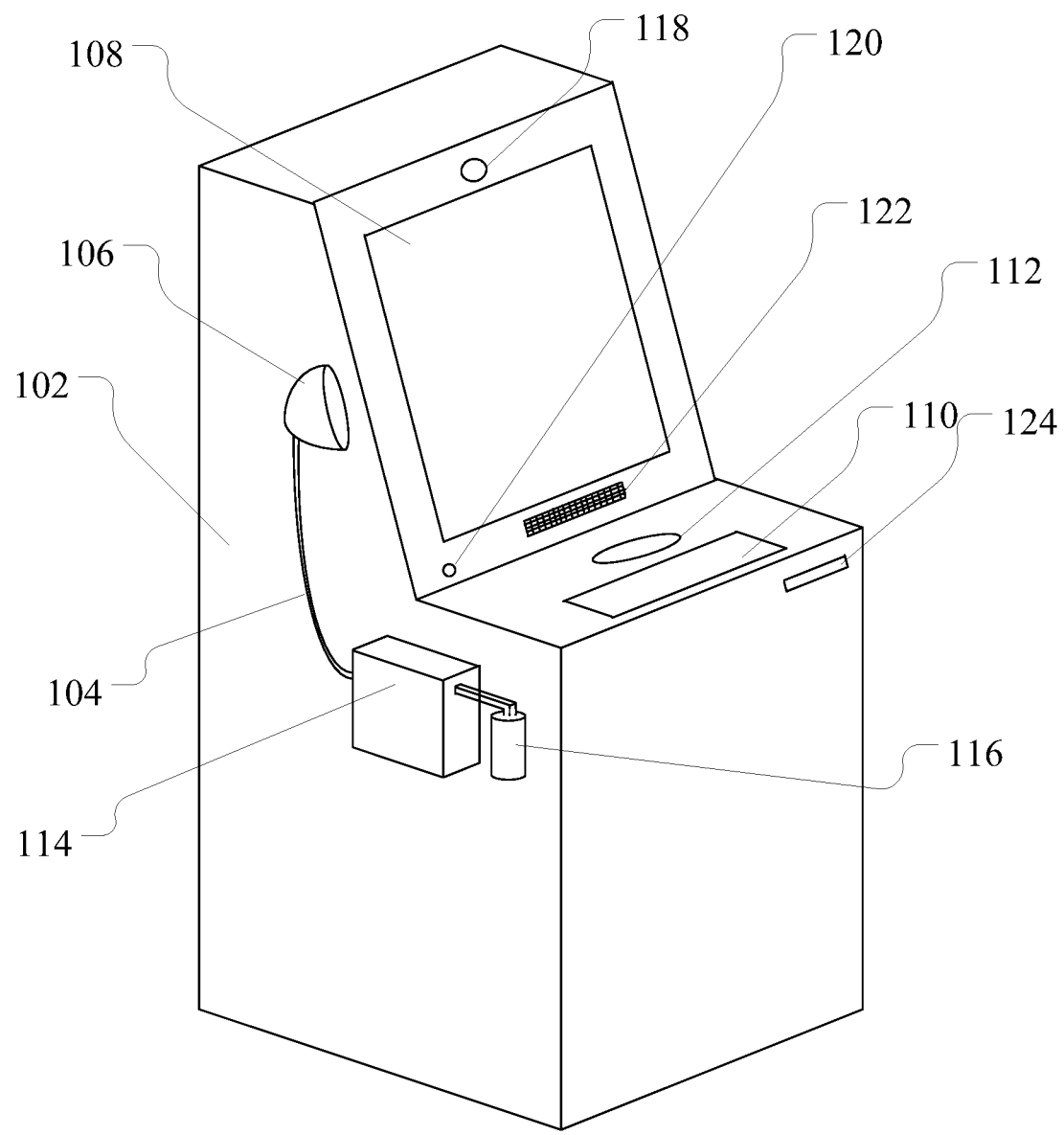

Some of the embodiments will be described in detail, with reference to the following figures, wherein like designations denote like members, wherein:

FIG. 1 illustrates the gas vending system for health application in an embodiment of the present invention.

Figure 2:
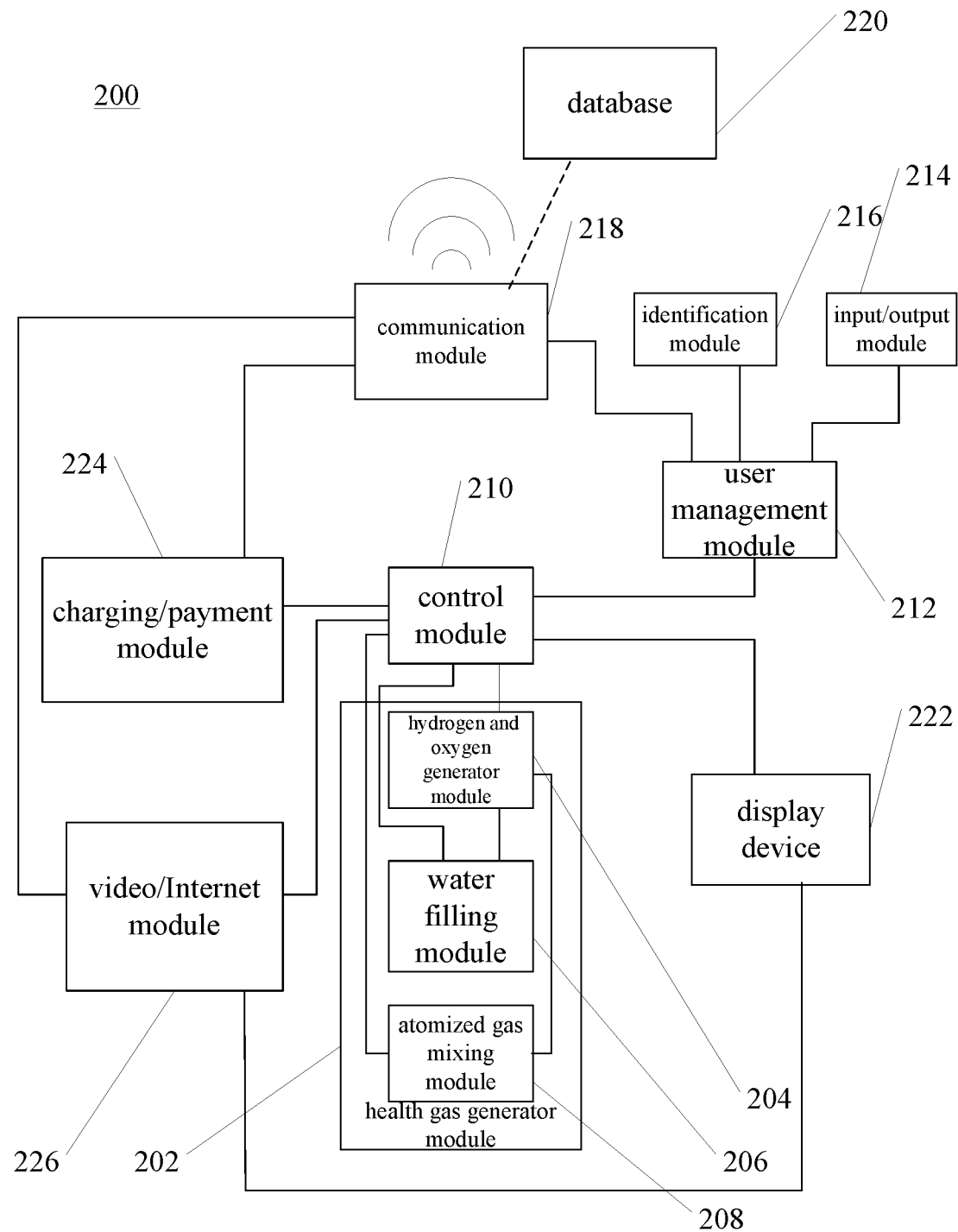

FIG. 2 illustrates the block diagram of the gas vending system for health application in an embodiment of the present invention.

DETAILED DESCRIPTION

A detailed description of the hereinafter described embodiments of the disclosed apparatus and method are presented herein by way of exemplification and not limitation with reference to the Figures. Although certain embodiments are shown and described in detail, it should be understood that various changes and modifications may be made without departing from the scope of the appended claims. The scope of the present invention will in no way be limited to the number of constituting components, the materials thereof, the shapes thereof, the relative arrangement thereof, etc., and are disclosed simply as an example of embodiments of the present invention.

Studies have found that there is an instable oxygen species (O—), also known as free radicals, in the human body. The free radicals are usually generated due to diseases, diet, environment and one's lifestyle, and the free radicals in the human body can be excreted in the form of water by reacting with the inhaled hydrogen. With this method, the amount of free radicals in the human body can be reduced, thereby restoring the body condition from an acidic state to an alkaline state, achieving an anti-oxidation, anti-aging and beauty health effect, and even eliminating chronic diseases. Furthermore, there are clinical experiments showing that for patients who need to inhale a high concentration of oxygen for a long time, the lung damage from the high concentration of oxygen can be ameliorated by inhaling hydrogen. According to the statement mentioned above, gas including hydrogen is extremely beneficial in a healthy gas, which can be generated by electrolyzing water.

Please refer to FIG. 1. FIG. 1 shows the gas vending system for health application in an embodiment of the present invention. According to some embodiments of the present invention, the gas vending system for health application 100 comprises a main body 102. The main body 102 comprises a relative device for generating a healthy gas that includes hydrogen and oxygen and mixes the gas mixture including hydrogen and oxygen with a volatile essential oil and an atomized medicinal liquid. The relative details will be explained later. The gas vending system for health application 100 further comprises a mask 106, connected to the relative device for generating a healthy gas comprised in the main body 102 through a pipe 104 to provide a healthy gas that includes hydrogen and oxygen for the user to breathe. The gas vending system for health application 100 further comprises a display device 108, such as a display panel which can be a liquid crystal display panel, light-emitting diode display panel or touch screen. The display device 108 is used to display relative information of the gas vending system for health application 100, wherein the relative information comprises: the usage state of the gas mixture including hydrogen and oxygen, atomized medicinal liquid, or volatile essential oil, such as flow rate, temperature, or pressure; and/or the using state of relative devices, such as the temperature, water level, or pressure of the electrolysis tank or the water bucket; and/or some relative alarm messages. For example, if the system has a gas leakage, the gas pressure of the gas mixture including hydrogen and oxygen is too high, the temperature of the devices are too high, or the water level of the electrolysis tank or the water bucket is abnormal; and/or the user interface is abnormal, such as the user management interface, functional options interface, toll interface, video playing interface, and Internet surfing interface. In some embodiments, the relative information of the user management interface displayed by the display device 108 includes an account, usage times, usage volume, or suggested setting. In another embodiment, the user management interface further connects with a database through connecting to the Internet, which is then used to connect the usage state or relative data of the user to the database in order to provide an exchanging function, such as a relative verification or an updating function. All the relative information can be displayed through the display device 108. In another embodiment, the video playing interface can play video or music for the user to enjoy while using the present invention. The relative information can also be displayed through the display device 108. The Internet surfing interface can provide a browser that allows the user to surf the Internet while using the present invention. The gas vending system for health application 100 further comprises an input/output device 110, such as a keyboard or touch panel, to allow the user to input relative messages, including an account, settings, or to select a function.

An emergency button 112 can further be configured in the gas vending system for health application 100 and can be electrically connected to the power supply. When the user meets an accidental situation, such as feeling uncomfortable, or an emergent change of the surrounding conditions, the user can directly press the emergency button 112 and the system will cut off the power supply. The gas vending system for health application 100 further comprises a medicinal liquid/essential oil supply module 114, which can be connected to the relative device for mixing the hydrogen and oxygen comprised in the main body 102. The medicinal liquid/essential oil supply module 114 can be connected to a medicinal liquid/essential oil bottle 116 outside. The medicinal liquid/essential oil bottle 116 can be provided by the user, or bought from the system vender and then connected to the medicinal liquid/essential oil supply module 114 according to the demand of the user. After that is done, the medicinal liquid/essential oil will then be atomized and mixed with hydrogen and oxygen by the system comprised in the main body 102 and is then provided for the user to breathe. It is worth noting that part of the medicinal liquid/essential oil can be provided by the system vender and configured in the gas vending system for health application 100 for the user to use fundamentally. The gas vending system for health application 100 further comprises an image acquisition device 118, such as a digital camera, used for acquiring the image of the user to log in through face identification, monitoring the usage image of the user, or other purposes.

The gas vending system for health application 100 further comprises a sound output device, comprising a loudspeaker 112, and/or earphone connector 120, which allows the gas vending system for health application 100 to output sounds. For example, when the gas vending system for health application 100 is abnormal, the present invention will not only display an alarm image through the display device 108 but also output alarm sounds through the loudspeaker 112 and/or the earphone connector 120. When the user is using the video playing interface or the Internet surfing interface of the gas vending system for health application 100, the image can still be displayed through the display device 108 and the sounds can be outputted through the loudspeaker 112 and/or the earphone connector 120. In addition, the gas vending system for health application 100 further comprises a card reader device 124, such as an IC chip card reader, a magnetic card reader, or a memory card reader. The card reader device 124 is used to read an IC chip card, magnetic card, or memory card for identifying the identity of the user, charge the system, read the relative information of the user, or read the information provided by the user and then importing the information into the system.

Please refer to FIG. 2. FIG. 2 shows the block diagram of the gas vending system for health application in an embodiment of the present invention. The gas vending system for health application 200 is similar to the statement mentioned above in FIG. 1. The main body 102 comprises a relative device for generating a healthy gas that includes hydrogen and oxygen and mixes the gas mixture including hydrogen and oxygen with a volatile essential oil and an atomized medicinal liquid. The healthy gas generator module 202 comprises: a hydrogen and oxygen generator module 204, a water filling module 206, and an atomized gas mixing module 208. Each module of the healthy gas generator module 202 is connected to the control module 210 individually and then monitored and controlled by the control module 210. For example, the hydrogen and oxygen generator module 204 comprises an electrolysis tank for generating the hydrogen and oxygen through electrolyzing water. The electrolysis tank can include a plate formed electrolysis tank or a double crested electrolysis tank. Because the electrolyzed water contained in the electrolysis tank will be consumed through electrolyzing, the hydrogen and oxygen generator module 204 is connected to the water filling module 206 in order to fill water into the electrolysis tank through the water filling module 206. The control module 210 will monitor the temperature of the electrolysis tank of the hydrogen and oxygen generator module 204, control the power supply of the electrolysis tank, and monitor the flow rate, temperature, and pressure of the generated hydrogen and oxygen and the water level, temperature, and pressure of the water filling module 206. All the monitored information mentioned above can be displayed through the display device 222 in order for the user or the system manager to watch or operate, where the alarm messages can still be displayed when the monitored information is abnormal. Additionally, the atomized gas mixing module 208 is connected to the hydrogen and oxygen generator module 204, wherein the hydrogen and oxygen generator module 204 can comprise an atomized/volatile gas mixing tank and an oscillator. A liquid is atomized through the oscillator in order to generate an atomized/volatile gas, and then is mixed with the hydrogen and oxygen to generate the healthy gas. The liquid, such as pure water, works as a base liquid for oscillating and atomizing; the liquid is selected from a group consisting of an essential oil, a medicinal liquid, pure water and a combination thereof; the atomized/volatile gas that is then produced is preferably a volatile essential oil, an atomized medicinal liquid, atomized water vapor or a combination of two or three of above-mentioned volatile/atomized items. The hydrogen and oxygen generator module 204 can be selectively switched on/off according to the demand of the user. That is to say, the hydrogen and oxygen generator module 204 can be switched on (for example, when actuating the oscillator) to provide the hydrogen and oxygen mixed with the atomized gas for the user to breathe, or the hydrogen and oxygen generator module 204 can be switched off (for example, when switching off the oscillator) to provide hydrogen and oxygen only for the user to breathe. According to the statement mentioned above, the hydrogen and oxygen generator module 204 can be connected to the medicinal liquid/essential oil supply module 114 in FIG. 1 in order to feed the medicinal liquid/essential oil into the hydrogen and oxygen generator module 204. According to the statement mentioned above, the healthy gas generated from the healthy gas generator module 202 can be connected to the pipe 104 in FIG. 1 to allow the user to breathe through the mask 106.

In some embodiments of the present invention, the gas vending system for health application 200 further comprises a user management module 212. The user management module 212 can be used to manage the logging in and out of the user, user/member account, and relative individual information of user (including ID, connecting information, individual health treatment information, using record or other individual information). As shown in the FIG. 2, the user management module 212 is individually connected to the input/output module 214, identification module 216, and communication module 218. According to the statement mentioned above, the user can log in/out through a card reader device 124 shown in FIG. 1, or an input/output module 214, including input/output device 100 shown in FIG. 1, such as a keyboard or touch panel. The relative information will be displayed on the display device 222. For example, the user can enter an account and certification password through the input/output device 110 shown in FIG. 1 in order to log in to the system, or in order to log in through the card reader device 124 and an IC chip card (such as a natural person chip card, or health insurance card). A user can also log in to the system through the identification module 216. For example, the image acquisition device 118 shown in FIG. 1 performs the facial identification for logging into the system. In some embodiments, the identification module 216 can include a finger print identification, voice print identification, retinopathy identification, or any other individual biological characteristics identification. User can also use individual hand-held devices (such as a smart phone) to identify the identity through the communication module 218 for logging into the system.

The user management module 212 can comprise a built-in database, used to store relative information of the user in order to correlatively certificate the logging in/out of the user mentioned above, or to relatively manage the information of the user, such as access right or deposit information. Users also load in or enter relative individual information through the input/output module 214 mentioned above, which includes ID, connecting information, individual healthy treatment information, or relative information of a debit/credit card. In some embodiments, the user management system can be connected to a cloud database 220 through the communication module 218 (such as broad-band network, wireless network, or mobile network). The database 220 can store all the relative information of the user mentioned above. Therefore, when the user is logging in/out, the user management module 212 can be connected to the database 220 through the communication module 218 to certify the user's identity/account. As shown in FIG. 2, the user management module 212 is also connected to the control module 210 to monitor and/or record the relative information of a user, including account access right or relative healthy treatment information, supply of the health gas of the system, or usage state. For example, the user management module 212 can receive an advised value or a controlled value for the flow rate of the healthy gas or the mixing volume of the atomized gas according to the health treatment information of the user. The control module 210 controls the flow rate of the healthy gas or mixing volume of the atomized gas, and the system will display an alarm message or shut down when the advised value or controlled value is exceeded.

In some embodiments of the present invention, the gas vending system for health application 200 further comprises a charging/payment module 224, connected to the control module 210 and the communication module 218. The charging/payment module 224 generates a toll after computing a value according to the received relative usage state of the user from the control module 210, including used volume of the healthy gas, hydrogen and oxygen, and atomized gas. The charging/payment module 224 is adapted to accept cash or charge a debit card, a credit card, or a deposit member card according to the toll. For example, the user can first pay some cash into the system through a cash register (not shown in the FIG.). The charging/payment module 224 will then charge according to the toll corresponding to the volume used. When the toll corresponding to the volume used is more than the cash the user paid before, the healthy gas will no longer be supplied. Similarly, if the user inserts the deposit member card/debit card into the card reader device 124 shown in FIG. 1 or uses the user management module 212 in order to enter relative information of the deposit member card/debit card, the charging/payment module 224 will charge according to the toll corresponding to the volume used. When the toll corresponding to the volume used is more than the balance remaining in the deposit member card/debit card, the healthy gas will no longer be supplied. If the user inserts their credit card into the card reader device 124 shown in FIG. 1 or uses the user management module 212 to enter relative information of their credit card, the charging/payment module 224 will charge according to the toll corresponding to the volume used. The charging action mentioned above uses the communication module 218 to connect to a financial system, such as a bank debit card system or credit card center in order to charge correspondingly.

In some embodiments of the present invention, the gas vending system for health application 200 further comprises a video/Internet module 226 that is connected to the control module 210, the display device 222, and a communication module 218. The video/Internet module 226 can provide video output through the display device 222 according to the demand of user. For example, playing videos, images, or music. The video/Internet module 226 can also allow the user to surf the Internet according to the demand of the user through the communication module 218 that is connected to the Internet. The video mentioned above can be played automatically through the control module 210. For example, the control module 210 can play the video automatically when the user is using the healthy gas according to the relative control options of the user management module 212 preset by the user. In another embodiment, the video/Internet module 226 can also predetermine some play modes to play automatically when the user is using the system. For example, the video/Internet module 226 can play a specific video if the specific atomized essential oil is selected to be used. Furthermore, the video/Internet module 226 can play a video automatically when nobody using the system, such as an advertisement video. The video played by the video/Internet module 226 can be built-in the system or downloaded from the Internet through the communication module 226.

To summarize the statement mentioned above, the gas vending system for health application of the present invention can use a charging/payment module to charge according to the toll that corresponds to the volume used by the user. The charging system is adapted to accept cash or charge a deposit member card/debit card/credit card conveniently. In addition, through the user management module and because the communication module is connected to the database, the usage state of the user can be completely recorded in order to provide references for the user or the manager of the system. The gas vending system for health application of the present invention further comprises a video/Internet module and display device for the user to watch videos or surf the Internet while it is being used, and simultaneously provides a comfortable situation for the user.

With the examples and explanations mentioned above, the features and spirits of the invention are hopefully well described. More importantly, the present invention is not limited to the embodiment described herein. Those skilled in the art will readily observe that numerous modifications and alterations of the device may be made while retaining the teachings of the invention. Accordingly, the above disclosure should be construed as limited only by the metes and bounds of the appended claims.

What is claimed is:
1. A gas vending system comprising:
   a healthy gas module to generate a healthy gas comprising:
      a gas generator configured to generate a gas comprising hydrogen through electrolyzing an electrolyzed water;
      a water filling module coupled to the gas generator for supplemental the electrolyzed water; and
      a gas mixing module coupled to the gas generator to receive the gas comprising hydrogen and then selectively mixing the gas comprising hydrogen with a vaporized gas generated from the gas mixing module to generate the healthy gas;

a control module coupled to the healthy gas module for monitoring a usage state of the healthy gas and generating a consumption signal of the healthy gas; and a user management module coupled to the control module and configured to connect with a cloud database which is remote from the gas vending system to transmit information to the cloud database, wherein the information transmitted to the cloud database comprises the usage state of the healthy gas and/or an abnormal condition of the gas vending system;

wherein the user management module is capable to receive from the cloud database an advised value for the flow rate of the healthy gas and/or a controlling signal for controlling the gas vending system.

2. The gas vending system of claim 1, further comprising a charging/payment module coupled to the control module for receiving the consumption signal of the healthy gas and generating a toll accordingly.

3. The gas vending system of claim 1, further comprising an identification module coupled to the user management module and configured to receive the information related to the user.

4. The gas vending system of claim 1, further comprising a display device coupled to the control module to display a relative information of the gas vending system.

5. The gas vending system of claim 4, further comprising a video module coupled to the display device and configured to provide a video output from an Internet to the display device.

6. A gas vending system comprising:

a healthy gas module to generate a healthy gas, wherein the healthy gas module comprises a gas generator to generate a gas comprising hydrogen and a gas mixing module for receiving the gas comprising hydrogen and then selectively mixing a vaporized gas generated from the gas mixing module with the gas comprising hydrogen to generate the healthy gas;

a control module coupled to the healthy gas module for generating a volume consumption signal for the healthy gas;

a charging/payment module coupled to the control module for receiving the volume consumption signal of the healthy gas and generating a toll accordingly;

an identification module configured to receive an information related to the user comprising individual health treatment information and using record; and a user management module coupled to the control module and the identification module, the user management module configured to transmit the information related to the user from the identification module to a cloud database which is remote from the gas vending system and being capable to receive from the cloud database an advised value for the flow rate of the healthy gas and/or a controlling signal for controlling the gas vending system.

* * * * *